(12) United States Patent
Lui et al.

(10) Patent No.: US 10,980,470 B2
(45) Date of Patent: Apr. 20, 2021

(54) CHIP FOR DETECTING ALLERGY, MANUFACTURING METHOD THEREOF AND A METHOD FOR DETECTING ALLERGY USING THEREFOR

(71) Applicant: Taichung Veterans General Hospital, Taichung (TW)

(72) Inventors: Ping-Wing Lui, Taichung (TW); Chin Hui Shen, Taichung (TW)

(73) Assignee: TAICHUNG VETERANS GENERAL HOSPITAL, Taichung (TW)

( * ) Notice: Subject to any disclaimer, the term of this patent is extended or adjusted under 35 U.S.C. 154(b) by 0 days.

(21) Appl. No.: 15/924,837

(22) Filed: Mar. 19, 2018

(65) Prior Publication Data
US 2018/0303401 A1    Oct. 25, 2018

(30) Foreign Application Priority Data

Mar. 21, 2017 (TW) .................................. 106109402
Mar. 19, 2018 (TW) .................................. 107109347

(51) Int. Cl.
*A61B 5/00* (2006.01)
*G01N 33/53* (2006.01)
(Continued)

(52) U.S. Cl.
CPC .............. *A61B 5/411* (2013.01); *B82Y 30/00* (2013.01); *C07K 16/40* (2013.01); *C07K 16/44* (2013.01); *G01N 33/5304* (2013.01); *G01N 33/54366* (2013.01); *G01N 33/6854* (2013.01); *B82Y 5/00* (2013.01); *C07K 16/42* (2013.01); *G01N 33/5047* (2013.01); *G01N 33/6893* (2013.01); *G01N 2800/24* (2013.01)

(58) Field of Classification Search
CPC ........ C07K 16/44; C07K 16/40; C07K 16/42; A61B 5/411; G01N 33/54366; G01N 33/5304; G01N 33/6854; G01N 2800/24; G01N 33/6893; G01N 33/5047; B82Y 30/00; B82Y 5/00
See application file for complete search history.

(56) References Cited

PUBLICATIONS

Liu et al. Electrochemical immunosensors for antibodies to peanut allergen Ara h2 using gold nanoparticle-peptide films. Anal. Chem. 2010, vol. 82, pp. 5865-5871. (Year: 2010).*

(Continued)

*Primary Examiner* — Shafiqul Haq
(74) *Attorney, Agent, or Firm* — Muncy, Geissler, Olds and Lowe, P.C.

(57) ABSTRACT

The present invention discloses an allergy detection chip, a preparation method thereof, and a method for detecting allergy therewith. The allergy detection chip comprises a substrate; a plurality of nanoprojections, disposed on a surface of the substrate; a plurality of gold nanoparticles, disposed on the surface of the substrate comprising the nanoprojections; a plurality of linkers, attached to the surface of each of the gold nanoparticles at one end respectively; and a plurality of antibodies, having a carboxyl end of a heavy chain covalently bonded to the other end of each of the linkers respectively. By means of the allergy detection chip disclosed in the present invention, whether a patient has high risk of allergy can be quickly detected, so as to reduce the risks faced by the patients and the healthcare personnel.

1 Claim, 10 Drawing Sheets (51) Int. Cl.
*G01N 33/543* (2006.01)
*B82Y 30/00* (2011.01)
*G01N 33/68* (2006.01)
*C07K 16/40* (2006.01)
*C07K 16/44* (2006.01)
C07K 16/42 (2006.01)
*B82Y 5/00* (2011.01)
*G01N 33/50* (2006.01)

(56) References Cited

PUBLICATIONS

Payne et al. Mast cell tryptase: a review of its physiology and clinical significance. Anaesthesia 2004, vol. 59, pp. 695-703. (Year: 2004).*
Tabbara, Khalid. Tear tryptase in vernal keratoconjunctivitis. Arch. Ophthalmol. 2001, vol. 119, pp. 338-342. (Year: 2001).*
Shen et al. Site-selective orientated immobilization of antibodies and conjuages for immunodiagnostics development. Methods 2017, vol. 116, pp. 95-111. (Year: 2017).*

* cited by examiner

CHIP FOR DETECTING ALLERGY, MANUFACTURING METHOD THEREOF AND A METHOD FOR DETECTING ALLERGY USING THEREFOR

BACKGROUND OF THE INVENTION

1. Field of the Invention

The present invention relates to a medical detection product, and particularly to an allergy detection chip, a preparation method thereof, and a method for detecting allergy therewith.

2. Description of the Related Art

General anesthesia can be effected only by administering multiple drugs at the same time, and these drugs may cause acute allergic reactions and even shock to the patient. Perioperative anaphylactic shock is a common emergency during anesthesia, which usually occurs within several minutes or even within 1 minute after the intravenous administration during the induction period. In general, the incidence of perioperative anaphylactic shock is 1:10,000 to 1:20,000 in Australia and 1:6000 in Norway.

According to the study, the causes of perioperative anaphylactic shock mainly comprise muscle relaxants, latex, and antibiotics (primary β-lactam antibiotics), and the three allergens are essential to the anesthetic and surgical procedures. Specifically, the muscle relaxant is to assist the placement of an endotracheal tube and facilitate the operation to progress smoothly; latex is a component in related medical products that are widely used at present; and preventive antibiotics are also routine for the operations at present. Latex allergies have received great attentions, and powder-free latex gloves are now used in most of the hospitals, resulting in a significant reduction in the chance of latex allergy during surgery. Therefore, the anaphylactic shock occurring during the induction of anesthesia is now mainly caused by muscle relaxants and antibiotics.

In order to reduce the risk of developing allergy during the anesthetic and surgical processes, the detection techniques currently used are mostly enzyme-linked immunosorbent assays (ELISAs) or the detection of immunoglobulin E level. However, ELISA is not only time consuming, but also requires high detection cost, such that it is inapplicable to patients in emergency situations; and no allergens are detected in advance for patients who are not suspected of drug allergic reactions. The immunoglobulin E level is irrelevant to the severity of clinical allergic reactions, and no primary cells causing allergy can be distinguished therewith. In other words, because of the lack of rapid and cost-effective allergy detection methods in current medical processes, both the patients and the medical personnel face unpredictable high risks during the surgical procedure.

SUMMARY OF THE INVENTION

The present invention mainly aims at providing an allergy detection chip, a preparation method thereof, and a method for detecting allergy therewith, whereby whether a patient has high risk of allergy can be quickly detected before or during a medical procedure, so as to reduce the risks faced by the patients and the healthcare personnel.

Another object of the present invention is to provide an allergy detection chip, a preparation method thereof, and a method for detecting allergy therewith, with which the medical detection cost and manpower can be reduced significantly.

To achieve the above objects, the present invention discloses an allergy detection chip, which comprises a substrate; a plurality of nanoprojections disposed on a surface of the substrate; a plurality of gold nanoparticles disposed on the surface of the substrate comprising the nanoprojections; a plurality of linkers, attached to the surface of each of the gold nanoparticles at one end respectively; and a plurality of antibodies, having a carboxyl end of a heavy chain covalently bonded to the other end of each of the linkers respectively.

Preferably, the antibody is an anti-tryptase antibody or an IgG antibody.

Preferably, each of the nanoprojections is regularly disposed on the substrate.

Preferably, each of the nanoprojections is hemispherical, and has a diameter of 50-700 nm.

Preferably, each of the linkers is an activated thiol molecule having a carboxyl group, for example, each of the linkers is activated mercaptoundecanoic acid (MUA).

The present invention provides a method for preparing the allergy detection chip, which comprises indirectly immobilizing an antibody to a substrate via a linker, where the linker is a long-chain molecule having a mercapto group at one end and an amido group at the other end; and the substrate has a plurality of regularly disposed gold electrodes on a surface.

Further, the method for preparing the allergy detection chip disclosed in the present invention comprises:

Step a: reacting a plurality of linkers with a surface of the substrate, to bond the linkers to the surface of the gold electrodes on the substrate with the mercapto end group;

Step b: activating a carboxyl end of the linkers, to allow the linkers to have an amido group;

Step c: indirectly immobilizing a predetermined concentration of an antibody to the surface of the substrate by reacting with the linkers and bonding to the amido group; and Step d: obtaining an allergy detection chip.

In an embodiment of the present invention, the linker is mercaptoundecanoic acid (MUA).

The antibody is an IgG antibody or an anti-tryptase antibody.

Step b comprises activating the carboxyl group of the linkers in an NHS/EDC solution.

In another embodiment, the method for preparing the allergy detection chip disclosed in the present invention further comprises, between Steps c and d, Step c1 of adding bovine serum albumin to react with the surface of the substrate.

Preferably, the gold electrodes on the substrate are nano-hemispherical, and have a diameter of 50-700 nm.

In an embodiment, the gold electrodes are prepared by sputtering. For example, the substrate has regularly disposed nano-hemispherical structures on a surface, and the gold nanoparticles are sputtered on the surface having the nano-hemispherical structures through a sputtering process, to form a nano-gold film having a thickness of 5-10 nm.

The substrate is made of an anodic aluminum oxide back barrier layer.

The substrate is made of a polymer material, for example, plastic.

Based on the allergy detection chip disclosed in the present invention, the present invention provides a method for rapidly detecting allergy during treatment, which comprises:

Step a: determining the impedance of an allergy detection chip according to claim 1, to obtain a first impedance value;

Step b: reacting a sample with the allergy detection chip, and determining the impedance, to obtain a second impedance value;

Step c: determining an impedance variation from the first impedance value and the second impedance value; and Step d: analyzing and comparing the impedance variation with an impedance standard curve of an intended antigen, to determine whether a subject providing the sample has risk of developing allergic reactions, where the impedance standard curve of an intended antigen has a value-at-risk of allergy, which corresponds to a minimum antigen concentration at which allergy occurs. When the impedance variation is greater than the value-at-risk of allergy, the subject providing the sample is indicated to have high risk of developing allergy, and when the impedance variation is less than the value-at-risk of allergy, the subject providing the sample is indicated to have low risk of developing allergy.

DETAILED DESCRIPTION OF THE PREFERRED EMBODIMENTS

The present invention discloses an allergy detection chip, which is used to determine whether a subject providing a specimen have high risk of developing allergy by detecting the electrical impedance variation of a chip through an electrochemical method. Further, the allergy detection chip disclosed in the present invention is configured to have an antibody or a biorecognition element such as a molecule recognizing a particular antigen immobilized onto a chip via a linker, where the chip is a substrate having nano structures.

By means of the allergy detection chip disclosed in the present invention, a user can get to know the risk of developing allergy or the risk of developing allergy to a substance that a subject providing a specimen has merely by comparing the impedance values before and after the allergy detection chip is reacted with the specimen and analyzing the impedance variation. Herein, the specimen is blood, saliva, body fluid or a mixture thereof.

The substrate disclosed in the present invention is prepared by an anodic aluminum oxide process and a sputtering process. In order to meet the requirement of mass production in the industry, a concave nano mold is prepared by an anodic aluminum oxide process and an electroforming process, and then mass production of a substrate having nanostructures can be achieved by an imprinting process.

Figure 1A:
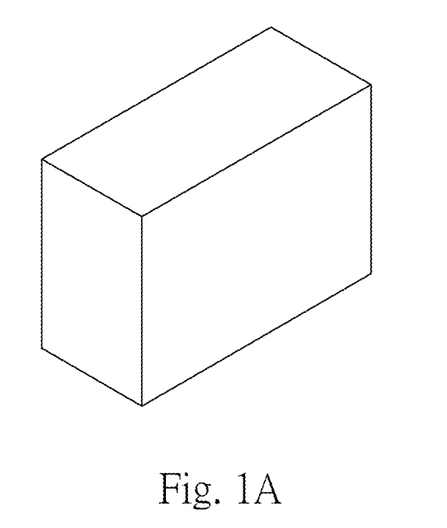
FIG. 1A is a view schematically showing a block aluminum substrate.
Figure 1B:
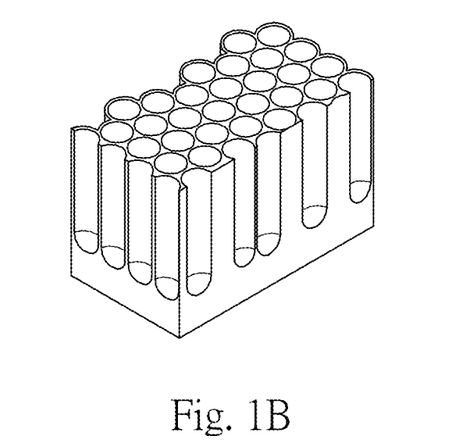
FIG. 1B is a view schematically showing an anodized block aluminum substrate.
Figure 1C:
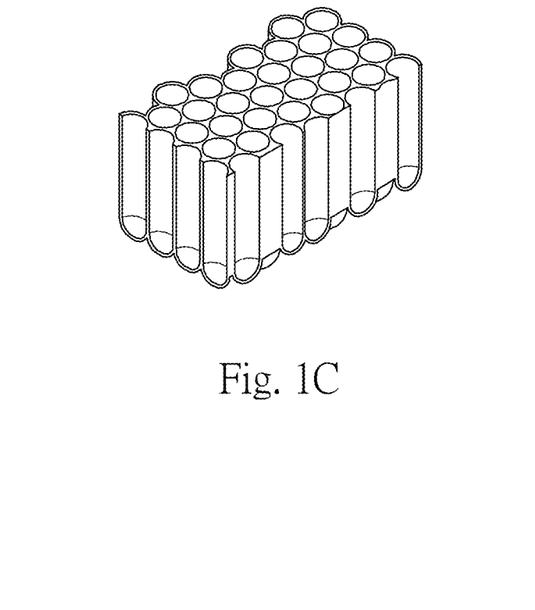
FIG. 1C is a view schematically showing an aluminum substrate having a plurality of nanoprojection structures.

For example, referring to FIGS. 1A to 1C, a block aluminum substrate is prepared into an aluminum material with uniform nanotubes by an anodic aluminum oxide process, and then a surface of the aluminum material that has not received the treatment with the anodic aluminum oxide process, is etched, for example, by a copper chloride and hydrogen chloride solution, to allow the aluminum substrate to have a plurality of nanoprojection structures on one side.

Figure 2:
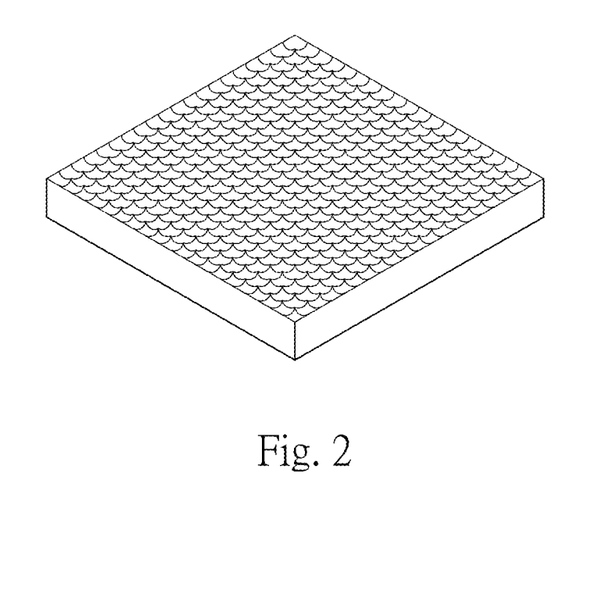
FIG. 2 is a view schematically showing a nickel mold having concave nanostructures.

In another embodiment of the present invention, a nano-gold film is further sputtered on the surface of the aluminum substrate having the nanoprojection structures, and then a nickel mold having a concave nanostructure is obtained through an electroforming process by using the aluminum substrate with the nanoprojection structures as a working electrode and a nickel-palladium material as an anode, as shown in FIG. 2. The nickel mold is used as a master mold and a polymer material is imprinted thereon, to reprint a substrate comprising the nanoprojection structures thereon. When the polymer material used is non-conducting, a gold nanoparticle sputtering process needs to be conducted to obtain a substrate comprising the nanostructures as disclosed in the present invention.

The linker disclosed in the present invention is a compound bearing a mercapto group, which is bonded to the surface of the gold particles through chemical adsorption by means of the mercapto end group, and has an van der Waals force between alkyl chains that allows the linker to have an angle of about 20-45 degrees with respect to the substrate having the gold particles. A long-chain thiol molecule can be aligned regularly on the substrate with gold particle. Through the linker, an antibody or other biological recognition elements can be indirectly attached to the detection substrate, for example, the substrate having nanostructures as disclosed in the present invention.

Figure 3:
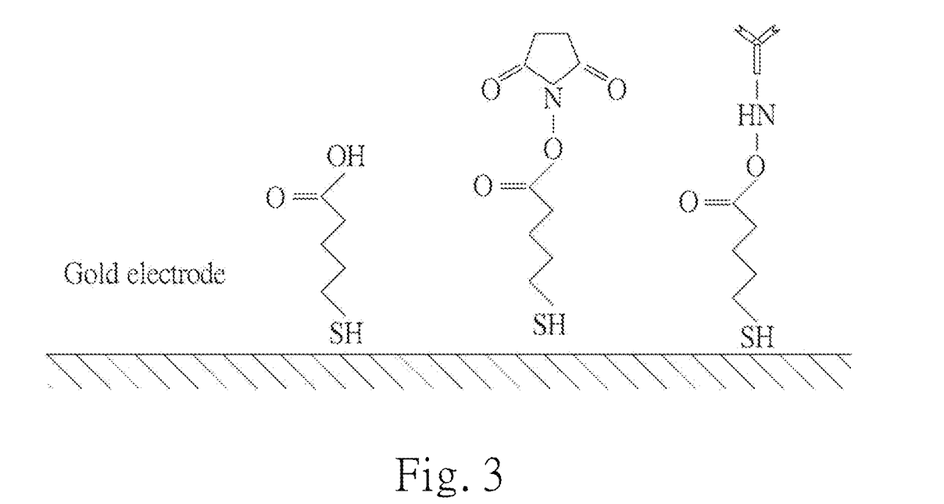
FIG. 3 is a view schematically showing the connection relationship between a linker disclosed in the present invention and an electrode and an antibody.

Specifically, referring to FIG. 3, in one embodiment of the present invention, the linker is 11-mercaptoundecanoic acid (11-MUA), which is modified onto the surface of the gold electrodes with the mercapto end, and has a carboxyl end that is activated by EDC/NHS to form an amide to which the biorecognition element or antibody is bonded, thereby achieving the ability to detect antigens or specific molecules.

In another embodiment of the present invention, the substrate comprising nanostructures is sputtered with gold nanoparticles, and then 11-MUA is modified onto the surface of the gold film, followed by activation of the carboxyl end of 11-MUA with EDC/NHS to form an amide. Moreover, bovine serum albumin is used as a blocking layer, such that the chip disclosed in the present invention is specific.

Hereinafter, to further confirm the disclosed effect of the present invention, the present invention will be further explained by way of examples with reference to the accompanying drawings.

Example 1: Preparation of Nanochip

Figure 4:
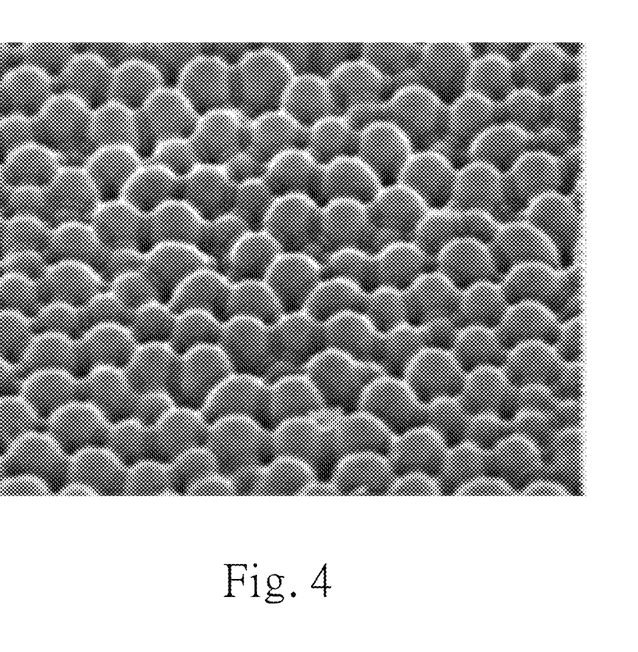
FIG. 4 shows the spherical 3D nanostructures observed under an electron microscope.

The surface of a 99.999% pure aluminum substrate as a test piece was sequentially washed with acetone, ethanol, and deionized water. Then, the washed pure aluminum test piece was positioned in a polishing solution consisting of perchloric acid and anhydrous ethanol at a volume ratio of 1:3, and electropolished for 2 min by applying a constant voltage of 20 V. After that, the test piece was washed with deionized water and blow dried with nitrogen. The electropolished aluminum substrate was positioned in a 0.3 M oxalic acid solution which was maintained at 0° C. by using a circulating cooling water bath, and anodized at a constant voltage of 90 V by using a power supply unit. After two hours, uniform nanotubes with a pore size of about 120 nm and a tube length of about 60 μm were obtained. The non-anodized back side of the pure aluminum substrate with the uniform array of nanotubes was etched with a cupric chloride and hydrogen chloride solution to obtain a barrier layer with 3D nanostructures having a diameter of about 110 nm. The back barrier layer was held in a Teflon fixture and subject to surface treatment in a 30 wt % phosphoric acid solution. The speed of the stirrer was 350 rpm, the operating temperature was 25° C., and the etching time was 50 minutes. As a result, obvious hemispherical 3D nanostructures were formed on the barrier layer, as shown in FIG. 4.

Example 2: Preparation of Mold

The surface of the anodic aluminum oxide membrane back barrier comprising hemispherical nanostructures prepared in Example 1 (referred to as anodic aluminum oxide membrane back barrier hereinafter) was sputtered with a nanogold film having a thickness of about 5-10 nm, and then electroforming was carried out in a nickel sulfaminate electroforming solution by using a nickel-palladium material as an anode and the anodic aluminum oxide membrane back barrier as a cathode (working electrode), where the electroforming time depends on the thickness of the nickel mold needed. After the electroforming, the electroformed area was removed, and the residual anodic aluminum oxide film was etched away with sodium hydroxide, to obtain a nickel mold having concave structures corresponding to the anodic aluminum oxide film back barrier.

Example 3: Reprint

The nickel mold prepared in Example 2 was used as a master mold, and heated and pressed onto the surface of a polycarbonate plastic by using a hot press, to form a nano-substrate. A titanium film and a gold film were sequentially sputtered on the surface of the obtained nanosubstrate, that is, the titanium film was disposed between the surface having the nanoprojections and the nanogold film. The related sputtering procedure was performed by using a sputter well known to those of ordinary skill in the art to which the present invention pertains, which is not detailed here again. When the sputtering procedure is performed with a current of 20 mA for a sputtering time of 220, 180, and 120 seconds respectively, the results are as shown in FIGS. 5A to 5C.

Figure 5A:
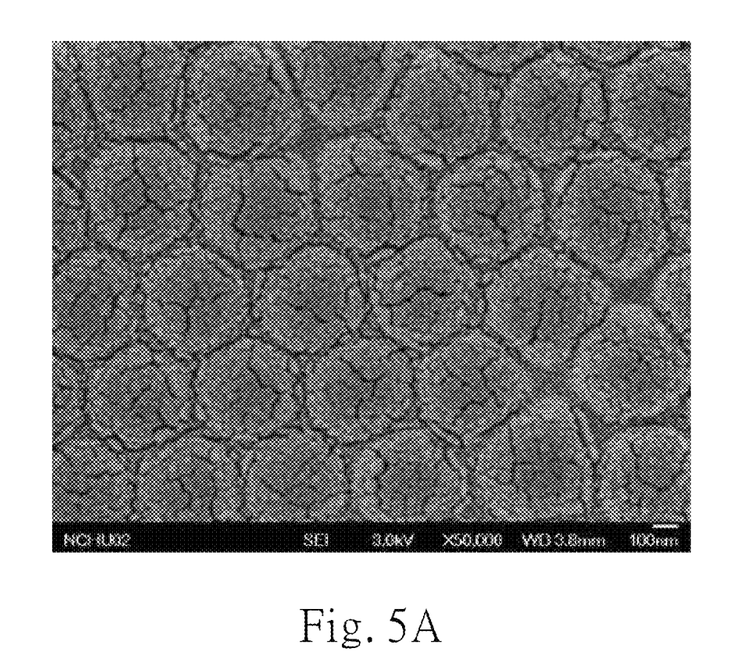
FIG. 5A shows the surface structure of an electrode formed after 220-second sputtering observed under an electron microscope.
Figure 5B:
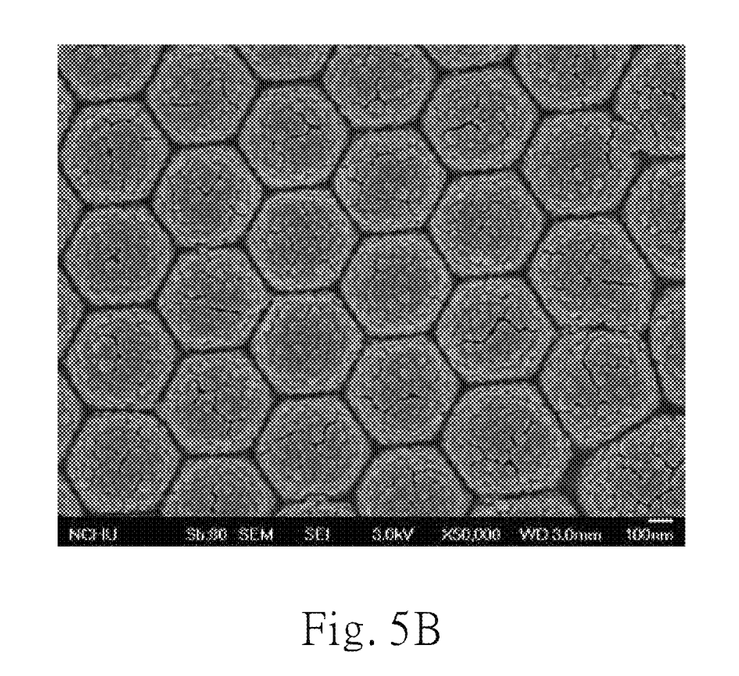
FIG. 5B shows the surface structure of an electrode formed after 180-second sputtering observed under an electron microscope.
Figure 5C:
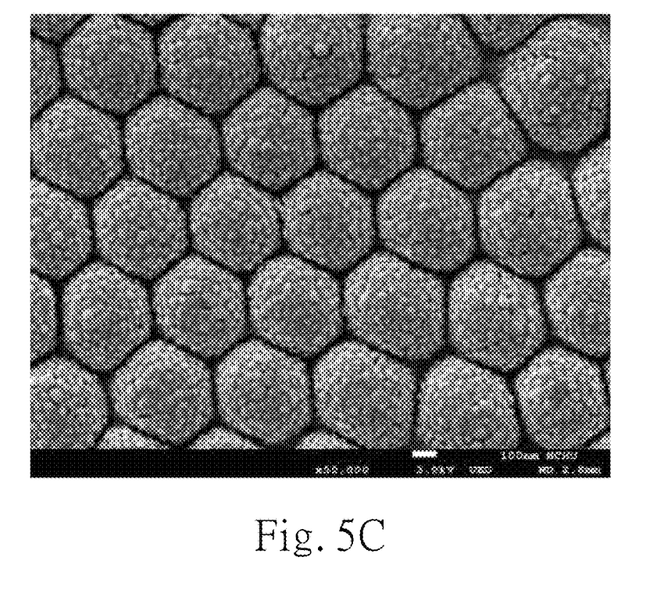
FIG. 5C shows the surface structure of an electrode formed after 120-second sputtering observed under an electron microscope.

As can be known from FIG. 5, when the sputtering time is too long, the thickness of the gold film may be too large, resulting in less obvious projections on the surface of the substrate and the cracking of the surface of the nanoprojections. When the sputtering time is 120 seconds, the gold particles of nanohemispherical surface are aligned evenly. It can be known that with a current of 20 mA and a sputtering time of 120 seconds, a substrate with uniformly sputtered and regularly aligned gold nanoparticles can be obtained.

In addition, to make the surface structure of the sputtered nano-substrate more planar, the sputtered nano-substrate was placed in a high-temperature furnace and treated at a constant temperature of about 120° C. for 1 hr, and then removed after cooling to room temperature.

Example 4: Chip Encapsulation

The planar surface of the sputtered nano-substrate was laminated on a printed circuit board, and then the sputtered nano-substrate was electrically connected by a wire. A sealing film of 2.5×2.5 cm2 having a central hole of 0.56 cm in diameter was covered on the nano-substrate, and then the nano-substrate was peripherally applied with AB glue and silica gel, to finish the encapsulation.

Example 5: Preparation of 11-MUA Solution 0.0021836, 0.010918, 0.021836, 1.0918, and 2.1836 g of 11-mercaptoundecanoic acid (11-MUA, molecular weight 218.36) were respectively formulated in 10 ml of 99.99% ethanol to give 1 mM, 5 mM, 10 mM, 100 mM, 500 mM, and 1000 mM 11-MUA solutions.

Example 6: Electrode Modification Test (I)

The gold electrodes were soaked for 16 hrs or more in 1 mM, 5 mM, 10 mM, 100 mM, 500 mM, and 1000 mM 11-MUA solutions respectively, and the impedance was measured in 5 mM $[Fe(CN)6]^{3-/4-}+0.1$ M KCl solution. The circuit component simulated value for the modified gold electrodes with various concentrations of 11-MUA solutions are shown in Table 1 below.

Further, the gold electrodes modified with various concentrations of 11-MUA solutions were separately activated with EDC/NHS, and then an anti-histamine antibody was attached, and modified with a blocking layer. The impedance was tested in a 5 mM $[Fe(CN)6]^{3-/4-}+0.1$ M KCl solution. The result is shown in FIG. 6.

Figure 6:
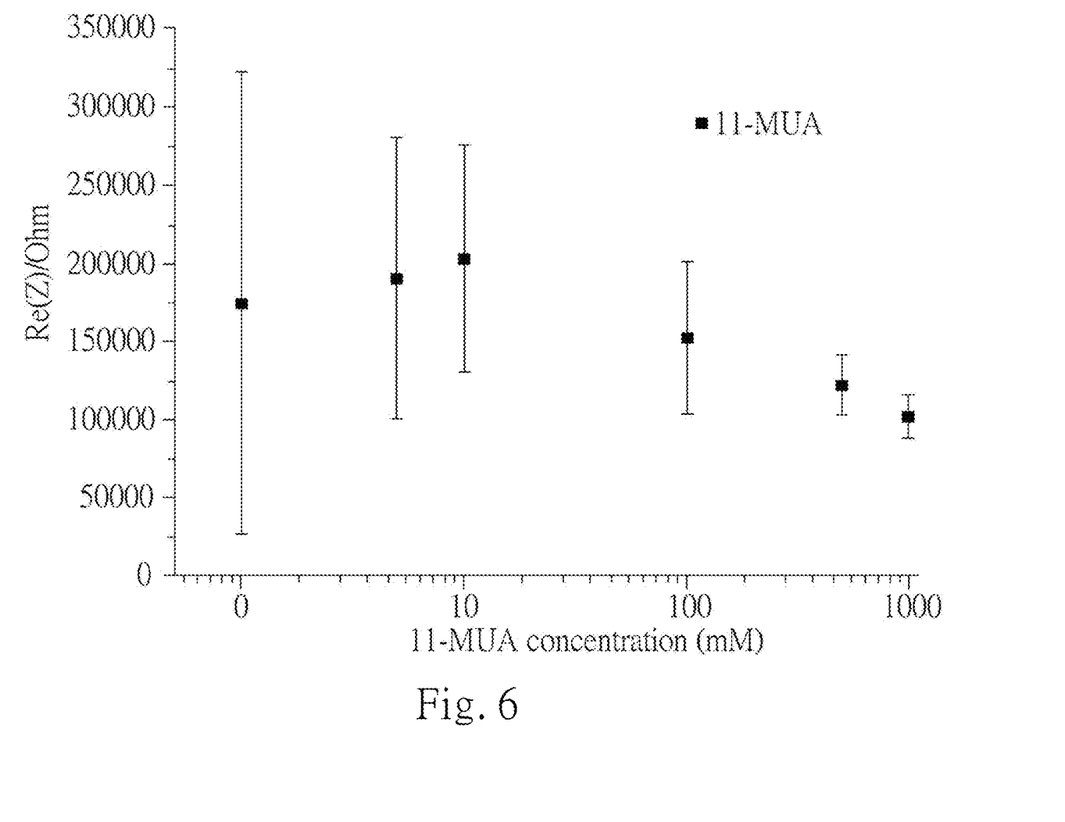
FIG. 6 shows the impedance test results in a 5 mM $[Fe(CN)6]^{3-/4-}$+0.1 M KCl solution after the sensing electrodes are modified with various concentrations of MUA which is activated with EDC/NHS and attached with an anti-histamine antibody.

As can be known from FIG. 6, when modified with low concentrations of 11-MUA (1 mM, 5 mM, and 10 mM), the mean equivalent resistance (Ret) is about 200,000, in which the standard deviation in the case of 1 mM 11-MUA is up to 147,000; the standard deviation in the case of 5 mM 11-MUA is 899,000; and the standard deviation in the case of 10 mM 11-MUA is 719,000. When modified with high concentrations of 11-MUA (100 mM, 500 mM, and 1000 mM), the mean equivalent resistance is about 100,000, and the standard deviation in the case of 500 mM and 1000 mM 11-MUA declines to 16.6 or lower, which is about half of the standard deviation in the case of 10 mM 11-MUA. Moreover, there is no significant difference between the equivalent impedances in the case of 500 mM and 1000 mM 11-MUA. It can be known that when the concentration of the 11-MUA solution reaches 500 mM, the thiol molecules on the electrode surface reaches saturation.

TABLE 1

Circuit component simulated value for the gold electrodes modified with 11-MUA

| 11-MUA Concentration (mM) | $R_S$ (Ω) | $R_{ct}$ (KΩ) |
|---|---|---|
| 1 | 82.2 ± 1.4 | 175.0 ± 147.0 |
| 5 | 80.4 ± 0.8 | 190.6 ± 89.9 |
| 10 | 79.3 ± 2.0 | 203.4 ± 71.9 |
| 100 | 81.2 ± 0.5 | 152.3 ± 48.5 |
| 500 | 80.2 ± 1.6 | 122.2 ± 16.6 |
| 1000 | 79.7 ± 1.4 | 102.6 ± 14.0 |

Example 7: Electrode Modification Test (II)

In this example, a set of electrodes modified by soaking were prepared as follows. The gold electrodes were soaked for 3 hrs in a 500 mM 11-MUA solution. An additional set of electrodes modified by titration were prepared as follows. 40 μL of a 500 mM 11-MUA solution was titrated over 30 min onto the surface of the gold electrode, and then the surface was washed with 99% ethanol. The titration process was repeated 1, 2, or 3 times. The current at the electrodes in each test group was respectively measured by cyclic voltammetry, in which the gold electrode was used as a working electrode, the Ag/AgCl electrode was used as a reference electrode, and platinum was used as a counter electrode, the electric potential was from −0.6 V-0.6 V, and the sweep rate was 100 mV/s. The test results are shown in FIG. 7.

Figure 7A:
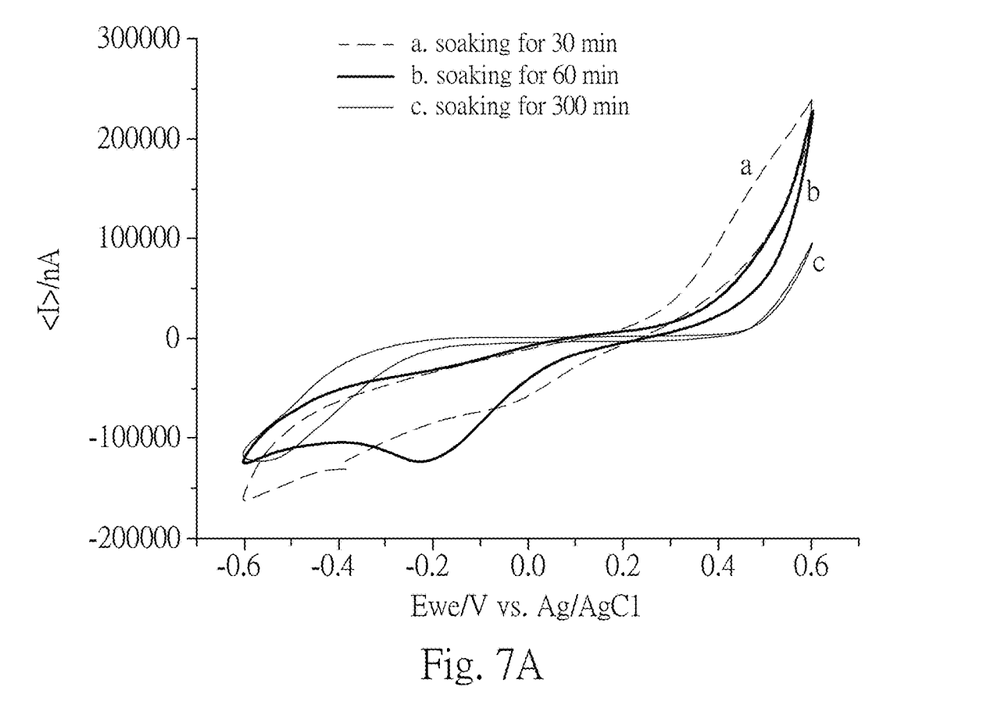
FIG. 7A shows a cyclic voltammogram of an electrode modified with MUA by soaking as measured by cyclic voltammetry.
Figure 7B:
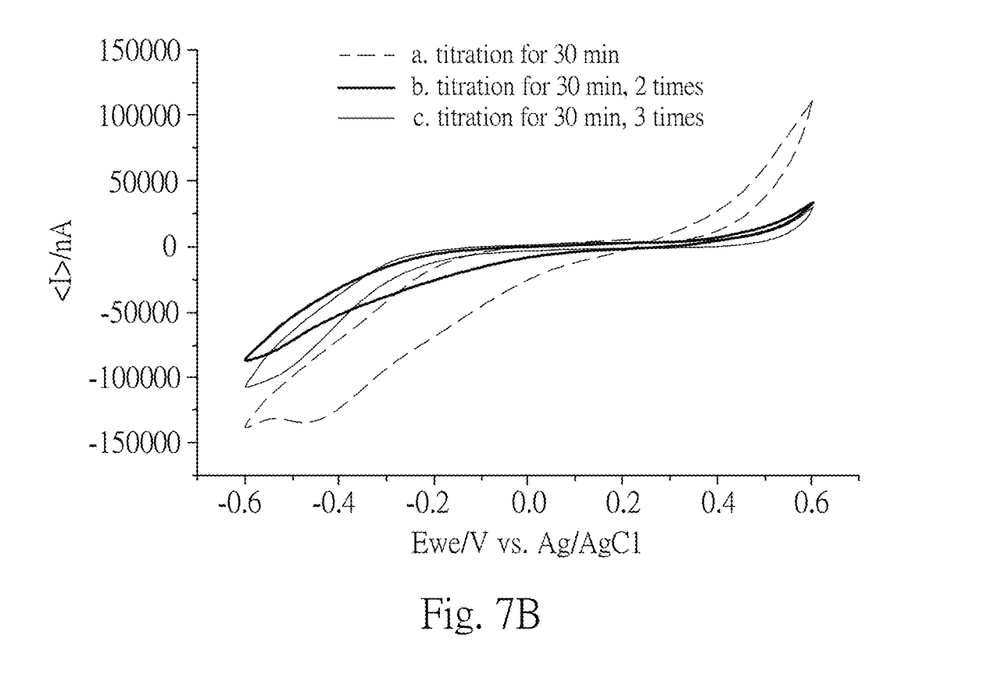
FIG. 7B shows a cyclic voltammogram of an electrode modified with MUA by titration as measured by cyclic voltammetry.

It can be known from FIG. 7A that when modified by soaking, a modification time of at least 3 hrs is needed to form upright and dense structures with 11-MUA on the surface of the electrode. It can be known from FIG. 7B that when modified by titration, a modification time of only 30 min allows the redox current on the surface of the electrode to decrease, and after at least 2 repeated titration processes, the 11-MUA is allowed to form upright and dense structures on the surface of the electrode, and no oxidation current is detected.

Example 8: Preparation of Allergy Detection Chip

As described in Examples 1 to 5, 20 μL of 11-MUA at a concentration of 500 mM was titrated onto the gold electrode on the surface of the encapsulated chip. After reaction at room temperature for 30 minutes, the surface was washed with 99% ethanol, and blow dried with nitrogen. 60 mM EDC and 4 mM 1-ethyl-3-[3-dimethylami-nopropyl] carbodiimide hydrochloride (NHS) were taken up in 15 mM 4-morpholineethanesulfonic acid hydrate (MES, pH 4.6) to form an EDC/NHS/MES mix solution. Then, the EDC/NHS/MES mix solution was titrated onto the chip surface for attachment reaction. After reaction, the chip was washed with deionized water, to obtain a modified encapsulated chip, in which the 11-MUA on the chip surface has an end amido functional group due to the activation by EDC/NHS.

The formulated antibody was titrated on the surface of the modified encapsulated chip to bond the antibody to the end group of 11-MUA, where the antibody is IgG, anti-tryptase antibody, and the like. After the antibody was attached, bovine serum albumin was dripped onto the chip surface to act as a blocking layer, so as to avoid the occurrence of nonspecific binding. In this way, an allergy detection chip disclosed in the present invention is obtained.

Example 9: Attachment of IgG Antibody

The IgG antibody was prepared into a 10000 ng/ml, 1000 ng/ml, 100 ng/ml, and 10 ng/ml solution, and each 40 μl of the solutions was titrated on the surface of the modified encapsulated chips for attachment, respectively. After reaction, the attachment of the IgG antibody was detected by impedance analysis. The result is shown in FIG. 8.

Figure 8:
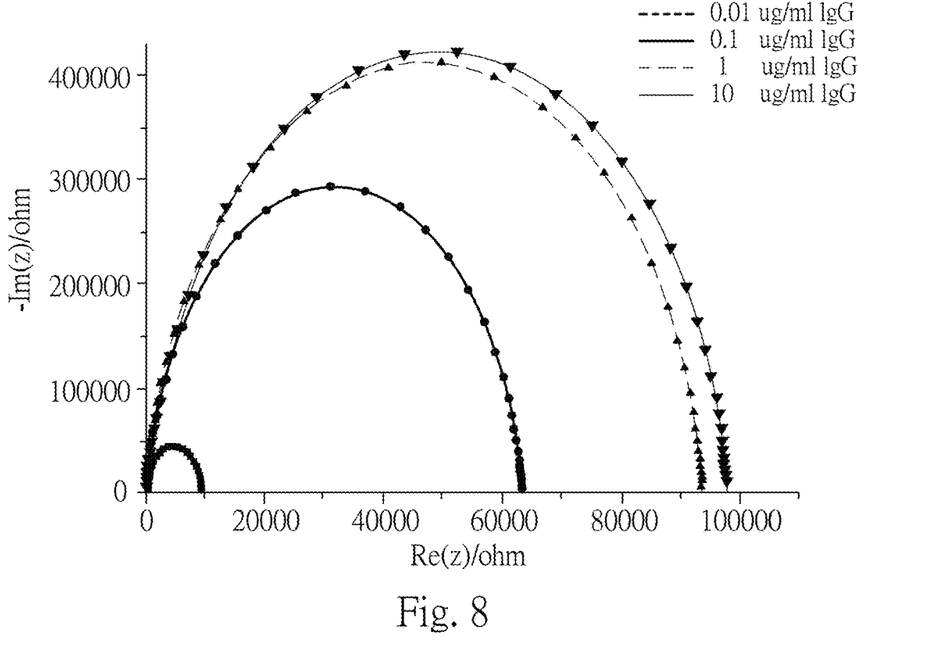
FIG. 8 shows a Nyquist plot obtained after various concentrations of an antibody (IgG) are attached.

From the results shown in FIG. 8, it can be seen that when the concentration of the IgG antibody is 1000 ng/ml, the impedance value is maximum, showing that the IgG antibody can be saturatedly attached to the activated end of 11-MUA at a concentration of 1000 ng/ml. Therefore, since no space is available for bonding on the chip, the impedance value cannot be further enhanced even if the concentration of the IgG antibody is increased.

Example 10: Preparation of Standard Curve of Histamine

Figure 9:
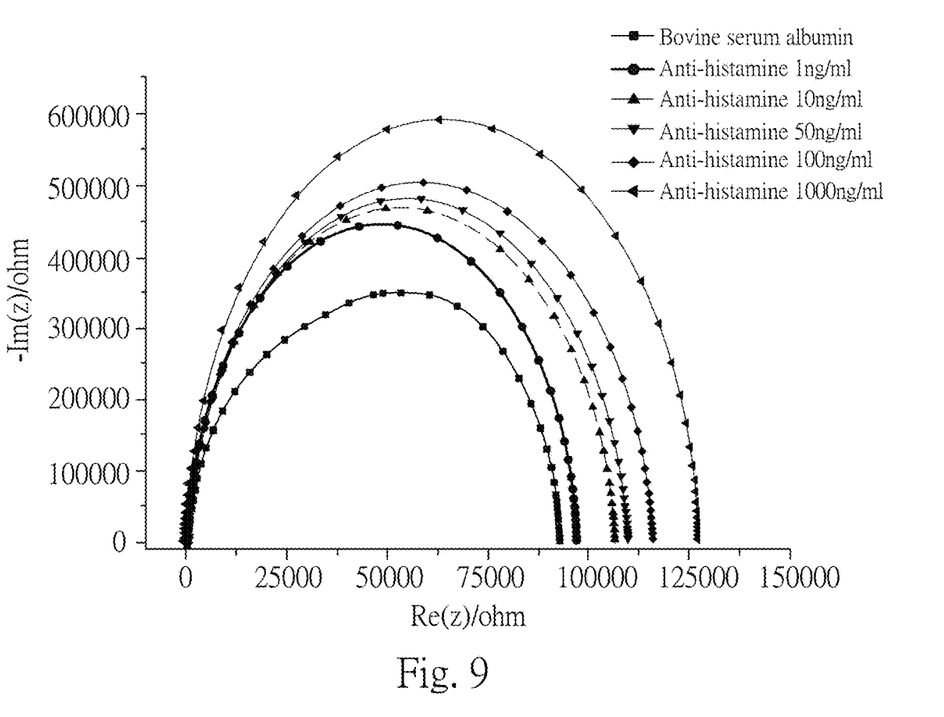
FIG. 9 shows a Nyquist plot obtained after various concentrations of histamine standard antigen are detected with the allergy detection chip comprising the IgG antibody disclosed in the present invention.
Figure 10:
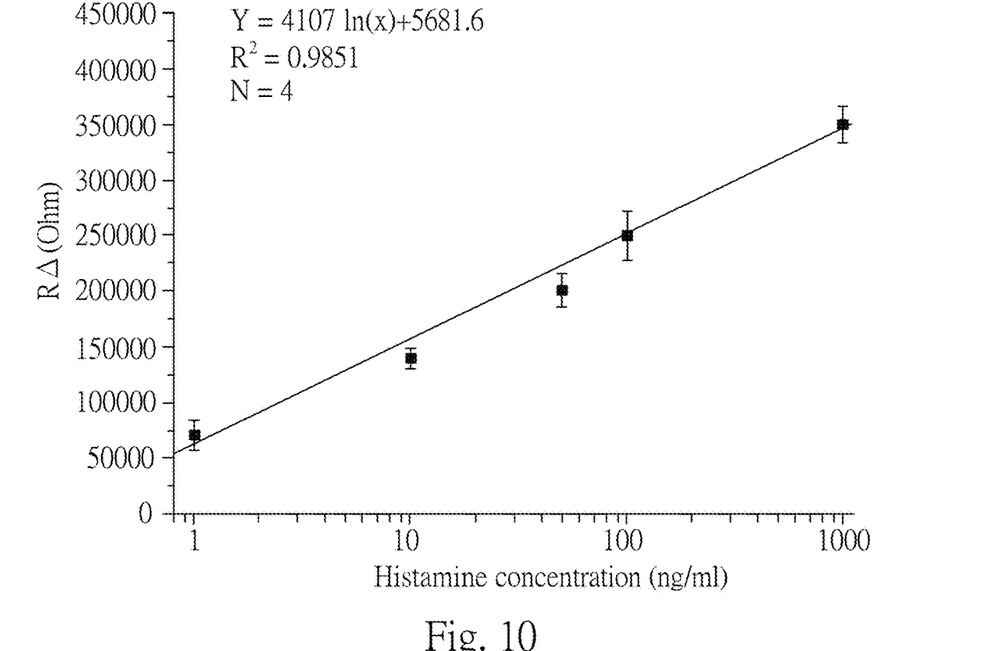
FIG. 10 shows a standard curve of histamine.

As described in Example 8, an allergy detection chip comprising the IgG antibody was prepared with a 1000 ng/ml IgG antibody solution. It is pointed out in literatures that the histamine concentration in the blood from normal (non-allergic) people is 1 to 10 ng/ml, and the histamine concentration in the blood from allergic people is 10 to 1000 ng/ml. Therefore, in this example, the histamine standard antigen were prepared into solutions of various concentrations, including 1 ng/ml, 10 ng/ml, 50 ng/ml, 100 ng/ml, and 1000 ng/ml. The solutions were respectively dripped to the allergy detection chip comprising the IgG antibody and reacted. The impedance was measured at a frequency ranging from 200 kHz to 20 mHz after the reaction. The measurement results are shown in FIG. 9 and Table 2, where ΔRCT is a difference between the impedance value after the chip is reacted with histamine and the impedance value before the chip is reacted with histamine (that is, the chip is modified only with 11-MUA and bovine serum albumin). Further, the data in Table 2 is plotted as a standard curve, as shown in FIG. 10. A regression equation of the standard curve is: y=702.91x+17332, where R2 is 0.9828.

TABLE 2

Histamine concentration, repeatability, impedance, standard deviation, coefficient of variation

| Histamine concentration (ng/ml) | Replications (n) | Δ $R_{ct}$ (Ω) | Standard deviation (Ω) | Coefficient of variation (%) |
|---|---|---|---|---|
| 1 | 4 | 7020 | 1296 | 18 |
| 10 | 4 | 13966 | 847 | 6 |
| 50 | 4 | 20192 | 1437 | 7 |
| 100 | 4 | 24955 | 2081 | 8 |
| 1000 | 4 | 35089 | 1654 | 4 |

It can be known that after the allergy detection chip disclosed in the present invention reacts with a specimen, the impedance value is detected, the impedance variation (ΔRCT) is calculated, and then the impedance variation is compared with the impedance curve of the standard histamine antigen as shown in FIG. 9, whereby whether a subject providing the specimen has high risk of allergic reactions can be determined quickly, and the concentration of histamine in the sample can be determined from the standard curve. In other words, it can be known from the allergy detection chip disclosed in the present invention and the literatures that when the impedance variation measured with the specimen is larger than about 13,000Ω, the subject providing the specimen has high risk of allergic reactions, and when the impedance variation measured with the specimen is larger than about 20000Ω, the subject providing the specimen has high risk of anaphylactic shock.

Example 11: Preparation of Standard Curve of Tryptase

Figure 11:
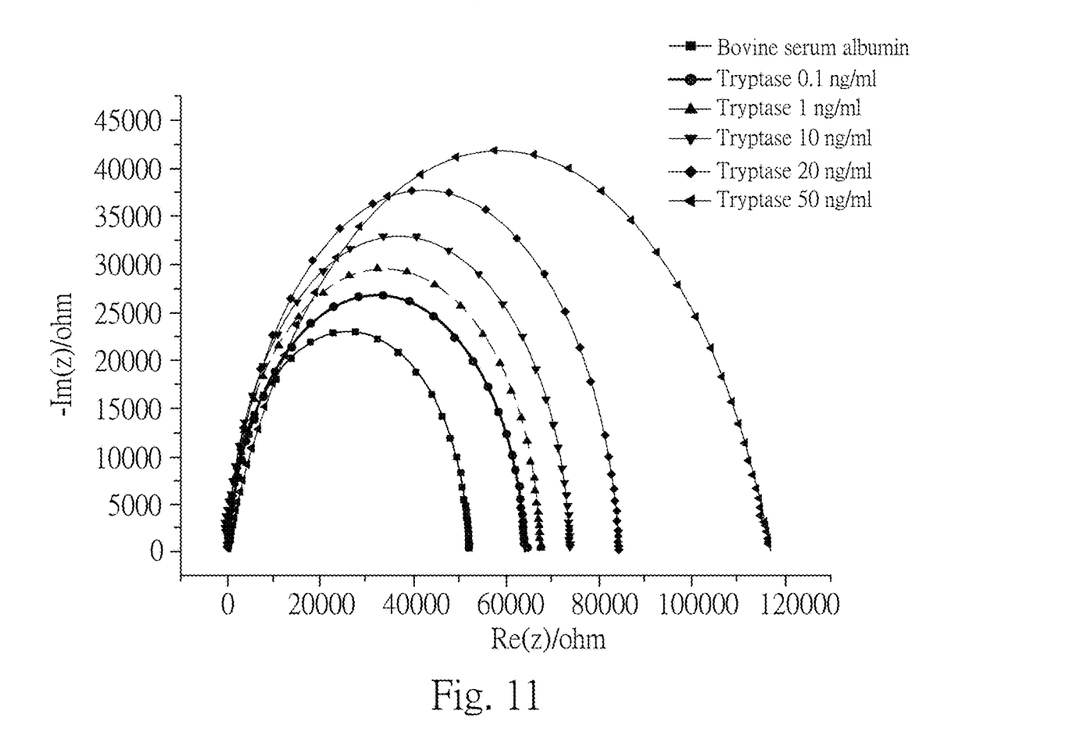
FIG. 11 shows a Nyquist plot obtained after various concentrations of tryptase are detected with the allergy detection chip comprising the anti-tryptase antibody disclosed in the present invention.

As described in examples above, a chip modified with an anti-tryptase antibody was prepared, and the impedance values of the chip attached with 11-MUA and bovine serum albumin respectively were measured. The chips modified with the anti-tryptase antibody were respectively reacted with various concentrations of tryptase standard solutions, including 0.1 ng/ml, 1 ng/ml, 10 ng/ml, 20 ng/ml, and 50 ng/ml. After the reaction, the impedance values of each of the chips were measured at a frequency ranging from 200 kHz to 20 mHz. The variation in the impedance values before and after the chip modified with the anti-tryptase antibody underwent attachment reaction with tryptase was calculated. The results are shown in Table 3 and FIG. 11.

Figure 12:
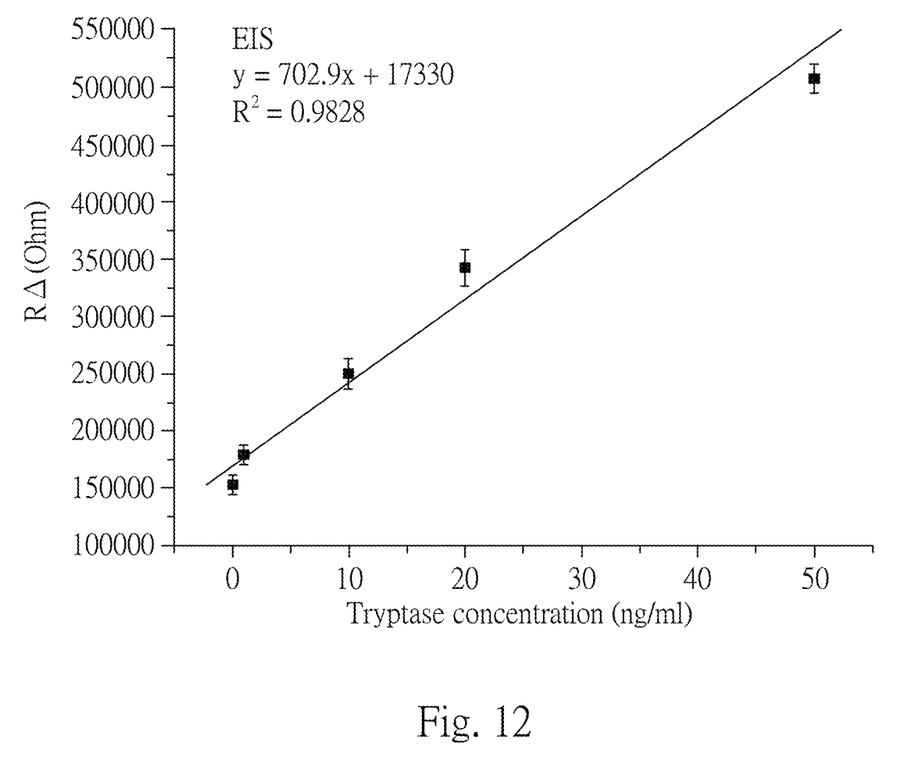
FIG. 12 shows a standard curve of tryptase.

Further, the data in Table 3 is plotted as a standard curve, as shown in FIG. 12. A regression equation of the standard curve is: y=702.9x+17330, where R2 is 0.9828.

TABLE 3

Tryptase concentration, repeatability, impedance, standard deviation, and coefficient of variation

| Tryptase concentration (ng/ml) | Replications (n) | $\Delta R_{ct}$ (Ω) | Standard deviation (Ω) | Coefficient of variation (%) |
| --- | --- | --- | --- | --- |
| 0.1 | 4 | 15298 | 829 | 5.4 |
| 1 | 4 | 17903 | 775 | 4.3 |
| 10 | 4 | 25008 | 1293 | 5.1 |
| 20 | 4 | 34243 | 1536 | 4.4 |
| 50 | 4 | 51214 | 634 | 1.2 |

It is pointed out in literatures that the tryptase concentration generally used to determine the allergic reaction in human is 11.4 ng/ml. Therefore, it can be known from above results that the standard curve of tryptase established from the reactions of the allergy detection chip modified with the anti-tryptase antibody disclosed in the present invention with tryptase in the above range of concentrations can be used to determine whether a subject providing a specimen has risk of allergy in future. For example, after the allergy detection chip modified with the anti-tryptase antibody is reacted with a specimen, if the resultant impedance variation is greater than 25000Ω, the subject providing the specimen is determined to have risk of allergy.

Example 12: Minimum Detection Limit of Tryptase

Figure 13:
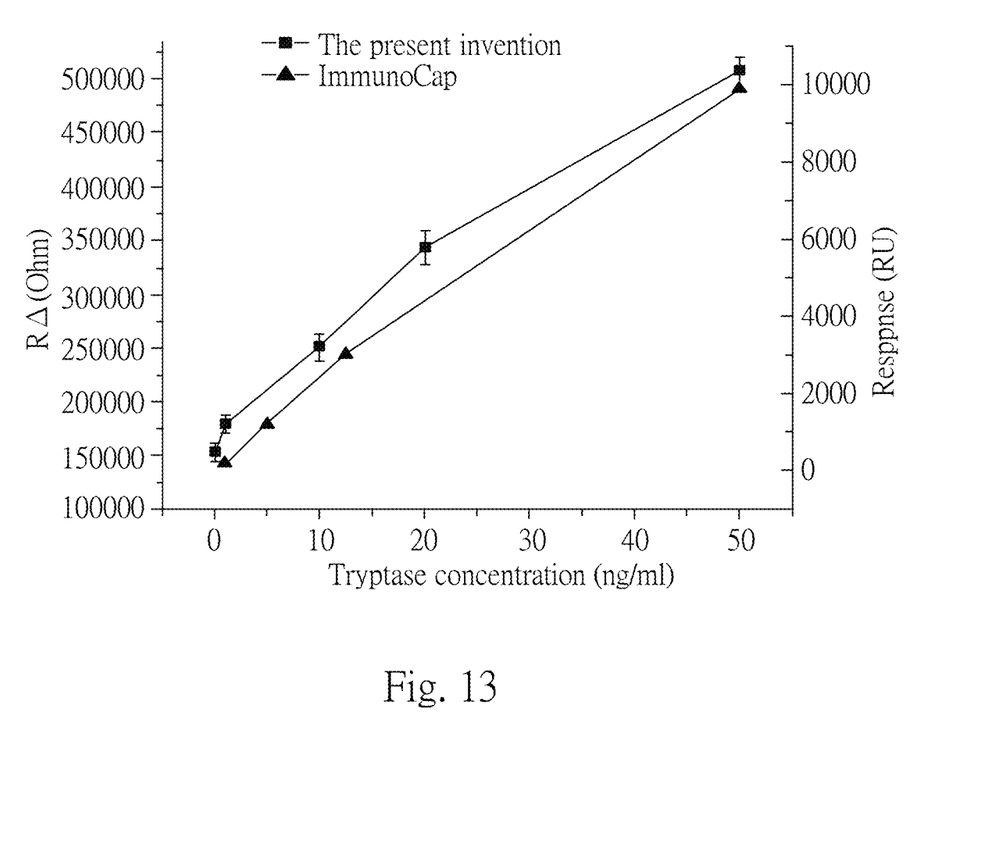
FIG. 13 shows the comparison of a standard curve of ImmunoCap for detecting tryptase and the standard curve as shown in FIG. 12.

According to the International Union of Pure and Applied Chemicals, a concentration corresponding to a detection limit that is the background plus the standard deviation thereof multiplied by 3 is the minimum detection limit. For the chip modified with bovine serum albumin (without the attachment reaction with an antigen), the average impedance measured is 50461Ω, and the standard deviation is 925Ω, so the minimum detectable impedance is 53236Ω. The average impedance of the allergy detection chip modified with the anti-tryptase antibody disclosed in the present invention after reaction with 1 pg/ml tryptase is 54722Ω. The impedance (54722Ω) obtained in the case of 1 pg/ml tryptase is quite close to the minimum detectable impedance (53236Ω). Therefore, the minimum detection limit of the allergy detection chip disclosed in the present invention for tryptase is 1 pg/ml Example 13: Comparison of the Present Invention with ImmunoCap At present, ImmunoCap is used to detect tryptase in clinic. Therefore, the standard curve of ImmunoCap for detecting tryptase and the standard curve obtained in Example 11 for the detection of tryptase using the allergy detection chip disclosed in the present invention are compared. The result is shown in FIG. 13. From the result shown in FIG. 13, it can be known that the R2 for the standard curve of ImmunoCap is 0.9971, and the R2 for the standard curve of the present invention is 0.9828, indicating that the R2 of the two are very close and close to 1.

It can be known that the allergy detection chip disclosed in the present invention is highly reliable in the detection of allergic reactions. In addition, in a conventional detection method with ImmunoCap, 200 μl of a specimen is needed, the detection time is 2.5 hrs, and a fluorescent label is needed, which increases the detection cost. In contrast, in the case of the allergy detection chip disclosed in the present invention, a detection effect comparable to that of the prior art can be obtained with only 40 μl of a specimen and 1-hr detection time, while the detection cost is effectively reduced.

Example 14: Treatment of Specimen

The blood was centrifuged to remove the buffy coat portion. A predetermined concentration of a muscle relaxant was added to react for a predetermined time, and then the supernatant was sampled as a test specimen.

Example 15: Detection of Risk of Allergy in a Subject

As described in Example 8, an allergy detection chip with an anti-tryptase antibody or an allergy detection chip with an IgG antibody was prepared. Blood was sampled from a subject and treated as described in Example 14, where the concentration of the muscle relaxant was 45.5 ng/ml.

First, the impedance of the allergy detection chip before the reaction was measured, and after the test specimen was reacted with the allergy detection chip for a predetermined time, the impedance of the allergy detection chip was further detected. The variation in the impedance values before and after the allergy detection chip was reacted with the test specimen was compared with the standard curve of tryptase or the standard curve of histamine (as shown in the examples above), to determine the concentration of tryptase or histamine in the specimen, with which whether the subject providing the specimen had high risk of allergy was determined. The results are shown in Tables 4 to 7 below. Further, the risks of allergic reactions that the subjects providing the specimens had were confirmed by a clinical allergy test kit (BAT), showing that the subjects providing specimen Nos. 1 and 2 had a negative allergy test result, and the subjects providing specimen Nos. 3 and 4 had a positive allergy test result. The test results were compared with the results shown in Tables 4 to 7 to verify the accuracy of the allergy test chip disclosed in the present invention.

From the results in Tables 4 and 5, it can be known that as detected by the allergy detection chip disclosed in the present invention, the subjects providing specimen Nos. 1 and 2 have no risk of allergy. It can be known from comparison with the detection result using the clinical allergy test kit that the allergy detection chip disclosed in the present invention does have the effect of determining whether a subject proving a specimen has the risk of allergy.

Furthermore, it can be known from the result in Table 4 that the concentration of an allergen or a compound, such as a muscle relaxant, decreases due to the degradation with the elapse of reaction time, causing the impedance value determined to decrease. This indicates that the impedance value determined with the allergy detection chip disclosed in the present invention is authentic and referable, and can be used to accurately reflect the risk of allergy that a subject proving a specimen has even in a short reaction time, thereby effectively improving the defect of time consuming of the existing clinical allergy detection technology.

From the results in Tables 6 and 7, it can be seen that as detected by the allergy detection chip disclosed in the present invention, the subjects providing specimen Nos. 1 and 2 have risk of allergy. The result is also consistent with the detection result using the clinical allergy test kit. Also, it can be known from the results in Tables 6 and 7 that by using the allergy detection chip disclosed in the present invention, the actual detection time is effectively shortened, which not only saves the manpower and material costs, but also make the use in clinic more in real time.

Also, as is well known to those skilled in the art to which the present invention belongs, the histamine in a specimen cannot currently be detected by using a commercially available kit or technique due to the rapid degradation of histamine. However, as can be clearly seen from the result in Table 8 below, the impedance after the reaction decreases with increasing reaction time, indicating that the histamine is degraded rapidly. This suggests that the result in Table 8 is authentic and referable. Further, considering the rapid degradability of histamine, whether a subject proving a specimen has high risk of allergy can be accurately determined and the histamine concentration in the specimen can also be determined by using the allergen detection chip disclosed in the present invention in a reaction time of 15 min.

From the above results, it can be seen that by using the allergy detection chip and the detection method therewith disclosed in the present invention, the risk of allergy that a subject has can be accurately determined, and the risk of allergy that a subject has can still be accurately evaluated with reduced allergen and reaction time of the specimen.

TABLE 4

Detection results of specimen No. 1 with an allergy detection chip comprising an anti-tryptase antibody at different times after reaction with a muscle relaxant

| Reaction time (min) | Initial impedance ($\Omega$) | Impedance after reaction ($\Omega$) | $\Delta R$ ($\Omega$) | Corresponding concentration |
|---|---|---|---|---|
| 25 | 64950.5 | 86198 | 21248.2 | <10 ng/ml |
| 180 | 115714.4 | 131171.2 | 15456.8 | 0.1 ng/ml |
| 360 | 144927.8 | 145946.8 | 1019 | 0.01 ng/ml |

TABLE 5

Detection results of specimen No. 2 with an allergy detection chip comprising an anti-tryptase antibody at 360 min after reaction with a muscle relaxant

| | Initial impedance ($\Omega$) | Impedance after reaction ($\Omega$) | $\Delta R$ ($\Omega$) | Corresponding concentration |
|---|---|---|---|---|
| Specimen No. 2 | 136100.1 | 141580.1 | 5480 | 0.03 ng/ml |

TABLE 6

Detection results of specimen No. 3 with an allergy detection chip comprising an anti-tryptase antibody at different times after reaction with a muscle relaxant

| Reaction time (min) | Initial impedance ($\Omega$) | Impedance after reaction ($\Omega$) | $\Delta R$ ($\Omega$) | Corresponding concentration |
|---|---|---|---|---|
| 15 | 57269 | 56296 | −973 | N |
| 30 | 57269 | 46926 | −10343 | N |
| 60 | 57269 | 78399 | 21130 | >10 ng/ml |
| 120 | 57269 | 84921 | 27652 | >10 ng/ml |

TABLE 7

Detection results of specimen No. 4 with an allergy detection chip comprising an anti-tryptase antibody at different times after reaction with a muscle relaxant

| Reaction time (min) | Initial impedance ($\Omega$) | Impedance after reaction ($\Omega$) | $\Delta R$ ($\Omega$) | Corresponding concentration |
|---|---|---|---|---|
| 15 | 66744 | 79290 | 12546 | N |
| 30 | 66744 | 82950 | 16206 | N |
| 60 | 66744 | 95997 | 29253 | >10 ng/ml |
| 120 | 66744 | 91542 | 24798 | >10 ng/ml |

TABLE 8

Detection results of specimen No. 4 with an allergy detection chip comprising an IgG antibody at different times after reaction with a muscle relaxant

| Reaction time (min) | Initial impedance ($\Omega$) | Impedance after reaction ($\Omega$) | $\Delta R$ ($\Omega$) | Corresponding concentration |
|---|---|---|---|---|
| 15 | 98146 | 116564 | 18418 | >10 ng/ml |
| 30 | 98146 | 97629 | −517 | N |
| 60 | 98146 | 90441 | −7705 | N |

What is claimed is:

1. A method for rapidly detecting allergy of a human subject, comprising:
    Step a: measuring a first impedance value of an allergy detection chip, wherein the allergy detection chip includes a plurality of linkers, wherein each of the linkers comprising a mercapto group at one end and an amido group at the other end and wherein the plurality of the linkers are attached covalently to a substrate via the mercapto group, and a plurality of a predetermined concentration of antibodies capable of reacting with tryptase or histamine and having a carboxyl end of a heavy chain covalently bonded to the amido group of the other end of each of the plurality of linkers that are attached to the substrate;

Step b: preparing a blood sample by adding a predetermined concentration of a muscle relaxant that are used in anesthesia to a blood sample obtained from the human subject;

Step c: reacting the prepared blood sample of step b having the muscle relaxant with the allergy detection chip, and measuring a second impedance value of the allergy detection chip after the reacting step c;

Step d: generating an impedance variation from the first measured impedance value and the second measured impedance value; and Step e: analyzing and comparing the impedance variation with an impedance standard curve of tryptase or histamine, to determine whether the human subject providing the blood sample has risk of developing allergy, wherein the impedance standard curve of tryptase or histamine has a value-at-risk of allergy, which corresponds to a minimum concentration at which allergy occurs, where when the impedance variation is greater than the value-at-risk of allergy, the human subject providing the blood sample is indicated to have high risk of developing allergy, and when the impedance variation is less than the value-at-risk of allergy, the human subject providing the blood sample is indicated to have low risk of developing allergy.

* * * * *